United States Patent [19]
Poustka et al.

[11] Patent Number: 6,133,005
[45] Date of Patent: Oct. 17, 2000

[54] TRANSKETOLASE-RELATED PROTEIN

[76] Inventors: Annemarie Poustka, Werderstrasse 36, Heidelberg, Germany, D-69120; Johannes Coy, In den scharzen Gärten 1, Grossostheim, Germany, D-63762

[21] Appl. No.: 09/011,074

[22] PCT Filed: Jul. 26, 1996

[86] PCT No.: PCT/DE96/01401

§ 371 Date: May 21, 1998

§ 102(e) Date: May 21, 1998

[87] PCT Pub. No.: WO97/05253

PCT Pub. Date: Feb. 13, 1997

[30] Foreign Application Priority Data

Jul. 27, 1995 [DE] Germany ............................ 195 27 552

[51] Int. Cl.$^7$ .............................. C12N 9/10; C12N 15/00; C12N 1/20; C12N 1/14; C07H 21/04
[52] U.S. Cl. ..................... 435/193; 536/23.2; 435/320.1; 435/252.3; 435/254.2
[58] Field of Search .................................. 435/69.1, 193, 435/320.1, 252.3; 536/23.2; 424/94.5

[56] References Cited

PUBLICATIONS

Branch, A.D. A good antisense molecule is hard to find. TIBS 23:45–50, Feb. 1998.

Schreier, H. The new frontier: Gene and oligonucleotide therapy. Antiinfective Drugs and Chemotherapy 13:1–13, 1995.

Abedinia et al., 1992, "Nucleotide and Predicted Amino Acid Sequence of a cDNA Clone Encoding Part of Human Transketolase," *Biochemical and Biophysical Research Communications* 183(3):1159–1166.

Bock et al., 1994, "Hepatitis B Virus Genome is Organized into Nucleosomes in the Nucleus of the Infected Cell," *Virus Genes* 8(3):215–229.

Butterworth et al., 1993, "Thiamine–Dependent Enzyme Changes in the Brains of Alcoholics: Relationship to the Wernicke–Korsakoff Syndrome," *Alcoholism: Clinical and Experimental Research* 17(5):1084–1088.

Coy et al., 1994, "Identification of Tissue–Specific Expressed Sequences in Human Band Xq28 with Complex Pig cDNA Probes," *Mammalian Genome* 5:131–137.

Coy et al., 1996, "Molecular Cloning of Tissue–Specific Transcripts of a Transketolase–Related Gene: Implications for the Evolution of New Vertabrate Genes,"*Genomics* 32:309–316.

Dietrich et al., 1991, "Molecular Cloning and Analysis of the Fragile X Region in Man," *Nucleic Acids Res.* 19:2567–2572.

Gottesman et al., 1981, "Role of sulA and sulB in Filamentation by Lon Mutants in *Escherichia coli* K–12," *J. Bacteriol.* 148(1):265–273.

Hochgeschwender, U., 1994, "Rapid Identification of Gene Sequences for Transcriptional Map Assembly by Direct cDNA Screening of Genomic Reference Libraries," *EMBL Database*, Accession No. U14622, Sequence Ref. HS14622.

Jung et al., 1993, "An Enzymatic and Immunological Analysis of Transketolase in Fibroblasts from Wernicke–Korsakoff Syndrome," *Journal of the Neurological Sciences* 114:123–127.

Khyse–Andersen, 1984, "Electroblotting of Multiple Gels: A Simple Apparatus without Buffer Tank for Rapid Transfer of Proteins from Polyacrylamide to Nitrocellulose," *J. Biochem. Biophys. Meth.* 10:203–209.

McCool et al., 1993, "Cloning of Human Transketolase cDNAs and Comparison of the Nucleotide Sequence of the Coding Region in Wernicke–Korsakoff and non–Wernicke–Korsakoff Individuals," *J. Biol. Chem.* 268(2):1397–1404.

F. Thomas and Th. Koller, 1981, "Unravelled Nucleosomes, Nucleosome Beads and Higher Order Structures of Chromatin: Influence of Non–histone Components and Histone H1," *J. Mol. Biol.* 149:709–733.

Thomas, K., 1995, "Human DNA Sequence from Cosmid 14B7 in Xq28 Containing Transketolase Pseudogene," *EMBL Database*, Accession No. Z49258, Sequence Ref. HS14B7.

*Primary Examiner*—Karen Cochrane Carlson
*Assistant Examiner*—Devesh Srivastava
*Attorney, Agent, or Firm*—Pennie & Edmonds LLP

[57] ABSTRACT

The present invention relates to a transketolase-related protein, a DNA encoding the same and a process for the preparation thereof. In addition, the invention concerns the use of the DNA and the protein as well as antibodies directed against the protein.

16 Claims, 4 Drawing Sheets

FIG. 1

```
1                                                                    GTCCTCCGCCACTGTGTCAGTGACAAGGTCACA
                                                                      V  L  R  H  C  V  S  D  K  V  T    11
34   GTTATTGGAGCTGGAATTACTGTGTATGAAGCCTTAGCAGCTGCTGATGAGCTTTCATCGTGTCATCGACCTGTTTACCATT
      V  I  G  A  G  I  T  V  Y  E  A  L  A  A  A  D  E  L  S  K  Q  D  I  F  I  R  V  I  D  L  F  T  I    44
133  AAACCCTCTGGATGTCGCCACCATCGTCTCCAGTGCAAAAGCCACAGAGGGCCGGATCATTACAGTGGAGGATCACTACCCGCAAGGTGGCATCGGGGAA
      K  P  L  D  V  A  T  I  V  S  S  A  K  A  T  E  G  R  I  I  T  V  E  D  H  Y  P  Q  G  G  I  G  E    77
232  GCTGTCTGCGCAGCCGTCTCCATGGATCCTGACATTCAGGTTCATTCGCTGGCAGTGTCCGGAGTGCCCCAGAGTGGGAAGTCCGAGGAATTGCTGGAT
      A  V  C  A  A  V  S  M  D  P  D  I  Q  V  H  S  L  A  V  S  G  V  P  Q  S  G  K  S  E  E  L  L  D    110
331  ATGTATGGAATTAGTGCCAGACATATCATAGTGGCCGTGAAATGCATGTTGCTGAACTAAAATAGCTGTTAGCCTGTCTTTTGGCCTCTCTTACCCTG
      M  Y  G  I  S  A  R  H  I  I  V  A  V  K  C  M  L  L  N                                              129
430  TGTTTATGTTTGTTCCAAAACCATCATTTAAATCTCTACTGTCACATTTGTTTCTTAAAAGCAAAGCCAGCTAACACCTTCATTCATCCCTAGTTCGG
529  AAATTCAAGCTAACTACTTACCCTTTAAACTGTCACTGCATATGCAAGTACCGCTCAATTTTTGGATCATTAAAGGGAGTTACACAACTTTTAAGTGA
628  AAAAAATAGGTAACAAAACAACCACCTGATAGTAAGTTTTCGATAAGACTATAGATAAGTGGTAGAGGTAATCAATTCTTCCGAAGTGTTTCCTTCGT
727  GAATAACTGGTAGAGGTAATAGTTTTTCAATGTATTTTCCTTCATGAGTAAAGAAAAATGTGAAGTATAGATTGAAGTATAGATTCCAGTAGCCTAGTTTCCACAGC
826  ACGATAACACCATGAGCGCCTACTGCTGTTCCCACCTTGTGTGCTGCCATCCCACCTGAGCTGCCAGCTGCCCTGGAATTCC
```

FIG. 2-1

```
1    GCTTCTATGAGGAGACCATGTGCCGAGGTCGTGTGCTGTGTTCTTCTGTGAGAAATGACCAGTTGCTGTGTCATGTCTGTCTTTCAGCCACCCTACATCA
100  TGTAGCAGTTCTTCTGAGATCATGTCTGTGCTGTTCTTCTTCTACATCATGAGGTACAAGCAGTCAGATCCAGAGAATCCGACAACGACCGATTTGTCCTC
1                 M   S   V   L   F   F   Y   I   M   R   Y   K   Q   S   D   P   E   N   P   D   N   R   F   V   L

199  GCAAAGAGACTGTCGTTTGTGGATGTGGCAACAGGATGGCTCGGACAAGGACTGGGAGTTGCATGTGGAATGGCCTTTGCTTCCTACTACAGTCGGACAAT
26    A   K   R   L   S   F   V   D   V   A   T   G   W   L   G   Q   G   L   G   V   A   C   G   M   A   Y   T   G   K   Y   F   D   R

298  GCCAGCTACCGGGTGTTCTGCCTCATGAGTGATGGCGAGTCCTCAGAAGGCTCTGTGTGGGAGGCAATGGCCTTTGCTTCCTACTACAGTCTGGACAAT
59    A   S   Y   R   V   F   C   L   M   S   D   G   E   S   S   E   G   S   V   W   E   A   M   A   F   A   S   Y   Y   S   L   D   N

397  CTTGTGGCAATCTTTGATGTGAACCGCCTGGGACACAGTGGTGCATTGCCCGCTGAAGCACTGCATAAACATCTATCAGAGGCGCTGCGAAGCCTTTGGG
92    L   V   A   I   F   D   V   N   R   L   G   H   S   G   A   L   P   A   E   H   C   I   N   I   Y   Q   R   R   C   E   A   F   G

496  TGGAACACTTATGTGGTGGACGGCCGGGACGTGGAGGCACTGTGCCAGGTATTCTGGCAGGCTTCTCAGGTGAAGCACAAGCCCACTGCTGTGGTGGCC
125   W   N   T   Y   V   V   D   G   R   D   V   E   A   L   C   Q   V   F   W   Q   A   S   Q   V   K   H   K   P   T   A   V   V   A

595  AAGACCTTCAAGGGCCGGGACATACAGCAGGAATCTTGACCCCAAGTATTGAGGATGACCAGCCCCCATTGAGGACTCACCTGGCTCTGGCTCTAAGCTG
158   K   T   F   K   G   R   G   T   P   S   I   E   D   A   E   S   W   H   A   K   P   M   P   R   E   R   A   D   A   I   I   K   L

694  ATTGAGAGCCAGATACAGACCAGCAGGAATCTTGACCCCAAGTATTGAGGATGACCAGCCCCCATTGAGGACTCACCTGGCTCTGGCTCTAAGCTG
191   I   E   S   Q   I   Q   T   S   R   N   L   D   P   Q   P   P   I   E   D   S   P   E   V   N   I   T   D   V   R   M   T   S   P

793  CCTGATTACAGAGTTGGTGACAGATAGCTACTCGGAAAAGCATGGCGTCTGGCTCTAAGCTGGCTACGCGAACAACAGAGTCGTTGTGCTGGAT
224   P   D   Y   R   V   G   D   K   I   A   T   R   K   A   C   G   L   A   L   A   K   L   G   Y   A   N   N   R   V   V   V   L   D

892  GGTGACACCAGGTACTCTCTGAGATATTCAACAAGGAGTACCTGAGTGCTTCATCGAGCGCTTCATCGAGTGCTTCATGGCTGAACAAAACATGTGAGCGTG
257   G   D   T   R   Y   S   T   F   S   E   I   F   N   K   E   Y   P   E   R   F   I   E   C   F   M   A   E   Q   N   M   V   S   V

991  GCTCTGGGCTGTGCCTCCGGTGACGACACATTGGTTCCCACTGTGCTTCCCACTGTGCTTGTGACGATGGCTTCCGAGGATATAGCCATGTTCCGA
290   A   L   G   C   A   S   R   G   R   T   I   A   F   A   S   T   F   A   A   F   L   T   R   A   F   D   H   I   R   I   G   G   L

1090 GCTGAGAGCAACATCAACATTATTGGTTCCCACTGTGGGGTATCGTGTGGTGACGATGGCTTCCGAGGATATAGCCATGTTCCGA
323   A   E   S   N   I   N   I   I   G   S   H   C   G   V   S   V   G   D   D   G   A   S   Q   M   A   L   E   D   I   A   M   F   R

1189 ACCATTCCCAAGTGCACGATCTTCTACCCAACTGATGCCGTCTCCACGGAGCATGCCGTGTGCTCTGGCAGCCAATGCCAAGGGGATGTGCTTCATCGG
356   T   I   P   K   C   T   I   F   Y   P   T   D   A   V   S   T   E   H   A   V   A   L   A   A   N   A   K   G   M   C   F   I   R

1288 ACCACCCGACCAGAACTATGGTTATTTACACCCACAAGAACGCTTTGAGATCGGACAGGCCAAGTCCTCCGACCACTGTGTCAGTGACAAGGTCACA
389   T   T   R   P   E   T   M   V   I   Y   T   P   Q   E   R   F   E   I   G   Q   A   K   V   L   R   H   C   V   S   D   K   V   T

1387 GTTATTGGAGCTGGAATTACTGTGTATGAAGCCTTAGCAGCTGCTGATGAGCTTTCGAAACAAGATATTTTATCCGTGTCATCGACCTGTTTACCATT
422   V   I   G   A   G   I   T   V   Y   E   A   L   A   A   A   D   E   L   S   K   Q   D   I   F   I   R   V   I   D   L   F   T   I
```

FIG. 2-2

```
1486  AAACCTCTGGATGTCGCCACCATCGTCTCCAGTGCAAAAGCCACAGAGGGCCGGATCATTACAGTGGAGGATCACTACCCGCAAGGTGGCATCGGGGAA
 455   K  P  L  D  V  A  T  I  V  S  S  A  K  A  T  E  G  R  I  I  T  V  E  D  H  Y  P  Q  G  G  I  G  E
1585  GCTGTCTGCGCAGCCGTCTCCATGGATCCTGACATTCAGGTTCATTCGCTGGCAGTGTCGGGAGTGCCCCAGAGTGGGAAGTCCGAGGAATTGCTGGAT
 488   A  V  C  A  A  V  S  M  D  P  D  I  Q  V  H  S  L  A  V  S  G  V  P  Q  S  G  K  S  E  E  L  L  D
1684  ATGTATGGAATTAGTGCCAGACATATCATAGTGGCCGTGAAAATGCTGCTGAACTAAAATAGCTGTTAGCCTTGGTCTTTTGGCCTCTCTTTACCCTG
 522   M  Y  G  I  S  A  R  H  I  I  V  A  V  K  C  M  L  L  N
1783  TGTTTATGTTGTTCCAAAACCATCATTAAATCTCTACTGTCACATTTGTTCTTAAAAGCAAAGCCAGCTAACACCTTCATTCATCCTAGTTCGG
1882  AAATTCAAGCTAACTACTTACCCTTTAAACTGCATATGCAAGTACCGCTCTAATTTTTGGATCATTAAAGGGAGTTACACAACTTTTAAGTGA
1981  AAAAACTAGGTAACACAAAACCACCACCTGATAGTAAGTTTTCTGATAAGATAAGTGGTAGAGGTAATCAATTCTTCCGAAGTGTTTCCTTCGT
2080  GAATAACTGGTAGAGGTAATAGTGCCTACGTCTTTTCCACCTTCATGAGTAAGAAAATGTGGATTGAAGTATAGATTCCAGTAGCCTAGTTTCCACAGC
2179  ACGATAACAGCATGACGCCTACGTCTGTCTGTGTGCCATCCCACCTGTCGCCACCTTCTGTGCTGCCCTGGAATTCCCTTCGCTGTTTGCCTT
2278  CATCTCCCTCCACGTTTGAGAGGCTGTCAGGCAGCAGCGAAAAGCTTGTTAGGATGTCCTGTGCTGCTGTGATGAGAGCCCTCCACACTGTACTGTTCAA
2377  GTCAATGTTAATAAAGCATTTCAAAACCAAAAAAAAAAAAAAAA
```

FIG. 3

```
1    GGCGTATCCATGCTCTCCAGGACAGCTGGAGCAGTGTAATTTCCTATCAAAAGTCCTCCGCCACTGTGTCAGTGACAAGGTCACA                                    27
          R  I  H  A  P  G  Q  L  E  Q  C  N  F  L  S  K  V  L  R  H  C  V  S  D  K  V  T
                                                    →
84   GTTATTGGAGCTGGAATTACTGTGTATGAAGCTTAGCAGCTGTGATGAGCTTTGAAACAAGATATTTTTATCCGTGTCATCGACCTGTTACCATT                          60
      V  I  G  A  G  I  T  V  Y  E  A  L  A  A  D  E  L  S  K  Q  D  I  F  I  R  V  I  D  L  F  T  I
183  AAACCCTGGATGTCGCCAGCCTGTCTCCAGTGCAAAGCCACAGTGGATCATTACAGTGGAGGATCACTACCCGCAAGGTGGCATCGGGGAA                              93
      K  P  L  D  V  A  T  I  V  S  S  A  K  A  T  E  G  R  I  I  T  V  E  D  H  Y  P  Q  G  G  I  G  E
282  GCTGTCTGCGCAGCCGTCTCCATGGATCCTGACATTCAGGTTCATTCGCTGGCAGTGTCGGAGTGCCCCAGAGTGGGAAGTCCGAGGAATTGCTGGAT                       126
      A  V  C  A  A  V  S  M  D  P  D  I  Q  V  H  S  L  A  V  S  G  V  P  Q  S  G  K  S  E  E  L  L  D
381  ATGTATGGAATTAGTGCAGACATATCATAGTGGCCGTGAAATGCATGTTGCTGAACTAAAAATAGCTGTTAGCCTTGGTCTTTTGGCCTCTCTTTACCCTG                     145
      M  Y  G  I  S  A  R  H  I  I  V  A  V  K  C  M  L  L  N
480  TGTTTATGTTTGTTCCAAAACCATCATTTAAATCTCTACTGTCACATTTGTTCTTAAAAGCAAAGCCAGCTAACACCTTCATTCATCCCTAGTTCGG
579  AAATTCAAGCTAACTACTTACCCTTTAAACTGTCACTGCATATGCAAGTACCGCTCTAAGTTTTGGATCATTAAAGGGAGTTACACAACTTTAAGTGA
678  AAAAAATAGGTAACAAAACAACACCTGATAGTAAGTTTTCTGATAAGACTATAGATAAGTGGTAGAGGTAATCAATTCTTCCGAAGTGTTTCCTTCGT
777  GAATAACTGGTAGAGGTAATAGTTTTTCATGTATTTCCTTCATGAGTAAAGAAAATGTGGATTGAAGTATAGATTCCAGTAGCCTAGTTCCACAGC
876  ACGATAACACCATGACGCCTACTGTCGTGTTCTGTGTGCTGCCATCCCCACCTTGGGCCTGCAGCTGCCCTGCCCTGGAATTCC
```

6,133,005

SEQUENCE LISTING

<160> NUMBER OF SEQ ID NOS: 9

<210> SEQ ID NO 1
<211> LENGTH: 908
<212> TYPE: DNA
<213> ORGANISM: Homo sapien
<220> FEATURE:
<221> NAME/KEY: CDS
<222> LOCATION: (1)...(387)

<400> SEQUENCE: 1

```
gtc ctc cgc cac tgt gtc agt gac aag gtc aca gtt att gga gct gga      48
Val Leu Arg His Cys Val Ser Asp Lys Val Thr Val Ile Gly Ala Gly
 1               5                  10                  15 att act gtg tat gaa gcc tta gca gct gct gat gag ctt tcg aaa caa      96
Ile Thr Val Tyr Glu Ala Leu Ala Ala Ala Asp Glu Leu Ser Lys Gln
                20                  25                  30 gat att ttt atc cgt gtc atc gac ctg ttt acc att aaa cct ctg gat     144
Asp Ile Phe Ile Arg Val Ile Asp Leu Phe Thr Ile Lys Pro Leu Asp
            35                  40                  45 gtc gcc acc atc gtc tcc agt gca aaa gcc aca gag ggc cgg atc att     192
Val Ala Thr Ile Val Ser Ser Ala Lys Ala Thr Glu Gly Arg Ile Ile
        50                  55                  60 aca gtg gag gat cac tac ccg caa ggt ggc atc ggg gaa gct gtc tgc     240
Thr Val Glu Asp His Tyr Pro Gln Gly Gly Ile Gly Glu Ala Val Cys
 65                  70                  75                  80 gca gcc gtc tcc atg gat cct gac att cag gtt cat tcg ctg gca gtg     288
Ala Ala Val Ser Met Asp Pro Asp Ile Gln Val His Ser Leu Ala Val
                 85                  90                  95 tcg gga gtg ccc cag agt ggg aag tcc gag gaa ttg ctg gat atg tat     336
Ser Gly Val Pro Gln Ser Gly Lys Ser Glu Glu Leu Leu Asp Met Tyr
                100                 105                 110 gga att agt gcc aga cat atc ata gtg gcc gtg aaa tgc atg ttg ctg     384
Gly Ile Ser Ala Arg His Ile Ile Val Ala Val Lys Cys Met Leu Leu
            115                 120                 125 aac taaaatagct gttagccttg gtcttttggc ctctttaccc tgtgtttatg          437
Asn tttgttccaa aaccatcatt taaatctcta ctgtcacatt ttgtttctta aaagcaaagc   497
cagctaacac cttcattcat ccctagttcg gaaattcaag ctaactactt acccttaaa    557 ctgtcactgc atatgcaagt accgctctaa tttttggatc attaaaggga gttacacaac   617
ttttaagtga aaaaaatagg taacaaaaca accacctgat agtaagtttt ctgataagac   677
tatagataag tggtagaggt aatcaattct tccgaagtgt ttccttcgtg aataactggt   737
agaggtaata gttttttcaa tgtatttcct tcatgagtaa agaaaatgtg gattgaagta   797
tagattccag tagcctagtt tccacagcac gataacacca tgacgcctac tgctgttccc   857
accttgggat tctgtgtgct gccatcccac ctgcagctgc cctggaattc c            908
```

<210> SEQ ID NO 2
<211> LENGTH: 129
<212> TYPE: PRT
<213> ORGANISM: Homo sapien

<400> SEQUENCE: 2

```
Val Leu Arg His Cys Val Ser Asp Lys Val Thr Val Ile Gly Ala Gly
 1               5                  10                  15

Ile Thr Val Tyr Glu Ala Leu Ala Ala Ala Asp Glu Leu Ser Lys Gln
                20                  25                  30
```

```
Asp Ile Phe Ile Arg Val Ile Asp Leu Phe Thr Ile Lys Pro Leu Asp
         35                  40                  45

Val Ala Thr Ile Val Ser Ser Ala Lys Ala Thr Glu Gly Arg Ile Ile
 50                  55                  60

Thr Val Glu Asp His Tyr Pro Gln Gly Gly Ile Gly Glu Ala Val Cys
 65                  70                  75                  80

Ala Ala Val Ser Met Asp Pro Asp Ile Gln Val His Ser Leu Ala Val
                 85                  90                  95

Ser Gly Val Pro Gln Ser Gly Lys Ser Glu Glu Leu Leu Asp Met Tyr
                100                 105                 110

Gly Ile Ser Ala Arg His Ile Ile Val Ala Val Lys Cys Met Leu Leu
            115                 120                 125

Asn

<210> SEQ ID NO 3
<211> LENGTH: 2418
<212> TYPE: DNA
<213> ORGANISM: Homo sapien
<220> FEATURE:
<221> NAME/KEY: CDS
<222> LOCATION: (121)...(1740)

<400> SEQUENCE: 3
gcttctatga ggagaccatg tgccgaggtc gtgtgctagg aagccagttg ctgtgagaaa        60
tgaccagtgt catgtctgtc tttcagccac cctacatcat gtagcagttc ttctgagatc       120 atg tct gtg ctg ttc ttc tac atc atg agg tac aag cag tca gat cca        168
Met Ser Val Leu Phe Phe Tyr Ile Met Arg Tyr Lys Gln Ser Asp Pro
 1               5                   10                  15 gag aat ccg gac aac gac cga ttt gtc ctc gca aag aga ctg tcg ttt        216
Glu Asn Pro Asp Asn Asp Arg Phe Val Leu Ala Lys Arg Leu Ser Phe
                 20                  25                  30 gtg gat gtg gca aca gga tgg ctc gga caa gga ctg gga gtt gca tgt        264
Val Asp Val Ala Thr Gly Trp Leu Gly Gln Gly Leu Gly Val Ala Cys
             35                  40                  45 gga atg gca tat act ggc aag tac ttc gac agg gcc agc tac cgg gtg        312
Gly Met Ala Tyr Thr Gly Lys Tyr Phe Asp Arg Ala Ser Tyr Arg Val
         50                  55                  60 ttc tgc ctc atg agt gat ggc gag tcc tca gaa ggc tct gtc tgg gag        360
Phe Cys Leu Met Ser Asp Gly Glu Ser Ser Glu Gly Ser Val Trp Glu
 65                  70                  75                  80 gca atg gcc ttt gct tcc tac tac agt ctg gac aat ctt gtg gca atc        408
Ala Met Ala Phe Ala Ser Tyr Tyr Ser Leu Asp Asn Leu Val Ala Ile
                 85                  90                  95 ttt gat gtg aac cgc ctg gga cac agt ggt gca ttg ccc gcc gag cac        456
Phe Asp Val Asn Arg Leu Gly His Ser Gly Ala Leu Pro Ala Glu His
                100                 105                 110 tgc ata aac atc tat cag agg cgc tgc gaa gcc ttt ggg tgg aac act        504
Cys Ile Asn Ile Tyr Gln Arg Arg Cys Glu Ala Phe Gly Trp Asn Thr
            115                 120                 125 tat gtg gtg gac ggc cgg gac gtg gag gca ctg tgc cag gta ttc tgg        552
Tyr Val Val Asp Gly Arg Asp Val Glu Ala Leu Cys Gln Val Phe Trp
        130                 135                 140 cag gct tct cag gtg aag cac aag ccc act gct gtg gtg gcc aag acc        600
Gln Ala Ser Gln Val Lys His Lys Pro Thr Ala Val Val Ala Lys Thr
145                 150                 155                 160 ttc aag ggc cgg ggc acc cca agt att gag gat gca gaa agt tgg cat        648
Phe Lys Gly Arg Gly Thr Pro Ser Ile Glu Asp Ala Glu Ser Trp His
                165                 170                 175
```

-continued

```
gca aag cca atg ccg aga gaa aga gca gat gcc att atc aaa tta att        696
Ala Lys Pro Met Pro Arg Glu Arg Ala Asp Ala Ile Ile Lys Leu Ile
        180                 185                 190 gag agc cag ata cag acc agc agg aat ctt gac cca cag ccc ccc att        744
Glu Ser Gln Ile Gln Thr Ser Arg Asn Leu Asp Pro Gln Pro Pro Ile
        195                 200                 205 gag gac tca cct gaa gtc aac atc aca gat gta agg atg acc tct cca        792
Glu Asp Ser Pro Glu Val Asn Ile Thr Asp Val Arg Met Thr Ser Pro
210                 215                 220 cct gat tac aga gtt ggt gac aag ata gct act cgg aaa gca tgc ggt        840
Pro Asp Tyr Arg Val Gly Asp Lys Ile Ala Thr Arg Lys Ala Cys Gly
225                 230                 235                 240 ctg gct ctg gct aag ctg ggc tac gcg aac aac aga gtc gtt gtg ctg        888
Leu Ala Leu Ala Lys Leu Gly Tyr Ala Asn Asn Arg Val Val Val Leu
                245                 250                 255 gat ggt gac acc agg tac tct act ttc tct gag ata ttc aac aag gag        936
Asp Gly Asp Thr Arg Tyr Ser Thr Phe Ser Glu Ile Phe Asn Lys Glu
                260                 265                 270 tac cct gag cgc ttc atc gag tgc ttt atg gct gaa caa aac atg gtg        984
Tyr Pro Glu Arg Phe Ile Glu Cys Phe Met Ala Glu Gln Asn Met Val
        275                 280                 285 agc gtg gct ctg ggc tgt gcc tcc cgt gga cgg acc att gct ttt gct       1032
Ser Val Ala Leu Gly Cys Ala Ser Arg Gly Arg Thr Ile Ala Phe Ala
        290                 295                 300 agc acc ttt gct gcc ttt ctg act cga gca ttt gat cac atc cgg ata       1080
Ser Thr Phe Ala Ala Phe Leu Thr Arg Ala Phe Asp His Ile Arg Ile
305                 310                 315                 320 gga ggc ctc gct gag agc aac atc aac att att ggt tcc cac tgt ggg       1128
Gly Gly Leu Ala Glu Ser Asn Ile Asn Ile Ile Gly Ser His Cys Gly
                325                 330                 335 gta tct gtt ggt gac gat ggt gct tcc cag atg gcc ctg gag gat ata       1176
Val Ser Val Gly Asp Asp Gly Ala Ser Gln Met Ala Leu Glu Asp Ile
                340                 345                 350 gcc atg ttc cga acc att ccc aag tgc acg atc ttc tac cca act gat       1224
Ala Met Phe Arg Thr Ile Pro Lys Cys Thr Ile Phe Tyr Pro Thr Asp
        355                 360                 365 gcc gtc tcc acg gag cat gct gtt gct ctg gca gcc aat gcc aag ggg       1272
Ala Val Ser Thr Glu His Ala Val Ala Leu Ala Ala Asn Ala Lys Gly
        370                 375                 380 atg tgc ttc att cgg acc acc cga cca gaa act atg gtt att tac acc       1320
Met Cys Phe Ile Arg Thr Thr Arg Pro Glu Thr Met Val Ile Tyr Thr
385                 390                 395                 400 cca caa gaa cgc ttt gag atc gga cag gcc aag gtc ctc cgc cac tgt       1368
Pro Gln Glu Arg Phe Glu Ile Gly Gln Ala Lys Val Leu Arg His Cys
                405                 410                 415 gtc agt gac aag gtc aca gtt att gga gct gga att act gtg tat gaa       1416
Val Ser Asp Lys Val Thr Val Ile Gly Ala Gly Ile Thr Val Tyr Glu
                420                 425                 430 gcc tta gca gct gct gat gag ctt tcg aaa caa gat att ttt atc cgt       1464
Ala Leu Ala Ala Ala Asp Glu Leu Ser Lys Gln Asp Ile Phe Ile Arg
        435                 440                 445 gtc atc gac ctg ttt acc att aaa cct ctg gat gtc gcc acc atc gtc       1512
Val Ile Asp Leu Phe Thr Ile Lys Pro Leu Asp Val Ala Thr Ile Val
        450                 455                 460 tcc agt gca aaa gcc aca gag ggc cgg atc att aca gtg gag gat cac       1560
Ser Ser Ala Lys Ala Thr Glu Gly Arg Ile Ile Thr Val Glu Asp His
465                 470                 475                 480 tac ccg caa ggt ggc atc ggg gaa gct gtc tgc gca gcc gtc tcc atg       1608
Tyr Pro Gln Gly Gly Ile Gly Glu Ala Val Cys Ala Ala Val Ser Met
                485                 490                 495
```

```
gat cct gac att cag gtt cat tcg ctg gca gtg tcg gga gtg ccc cag    1656
Asp Pro Asp Ile Gln Val His Ser Leu Ala Val Ser Gly Val Pro Gln
        500                 505                 510 agt ggg aag tcc gag gaa ttg ctg gat atg tat gga att agt gcc aga    1704
Ser Gly Lys Ser Glu Glu Leu Leu Asp Met Tyr Gly Ile Ser Ala Arg
    515                 520                 525 cat atc ata gtg gcc gtg aaa tgc atg ttg ctg aac taaaatagct         1750
His Ile Ile Val Ala Val Lys Cys Met Leu Leu Asn
530                 535                 540 gttagccttg gtcttttggc ctctttaccc tgtgttatg tttgttccaa aaccatcatt   1810
taaatctcta ctgtcacatt ttgtttctta aaagcaaagc cagctaacac cttcattcat  1870
ccctagttcg gaaattcaag ctaactactt acccttaaa ctgtcactgc atatgcaagt   1930
accgctctaa tttttggatc attaaaggga gttacacaac ttttaagtga aaaaaatagg  1990
taacaaaaca accacctgat agtaagtttt ctgataagac tatagataag tggtagaggt  2050
aatcaattct tccgaagtgt ttccttcgtg aataactggt agaggtaata gtttttttcaa 2110 tgtatttcct tcatgagtaa agaaaatgtg gattgaagta tagattccag tagcctagtt  2170
tccacagcag gataacagca tgaggcctac tgctgttccc accttcggat tctgtgtgct  2230
gccatcccac ctgcagctgc cctggaattc ccttcgctgt ttgccttcat ctccctccac  2290
gtttgagagg ctgtcaggca gcagcgaaag cttgttagga tgtcctgtgc tgcttgtgat  2350
gagagcctcc acactgtact gttcaagtca atgttaataa agcatttcaa aaccaaaaaa  2410
aaaaaaaa                                                           2418

<210> SEQ ID NO 4
<211> LENGTH: 540
<212> TYPE: PRT
<213> ORGANISM: Homo sapien

<400> SEQUENCE: 4

Met Ser Val Leu Phe Phe Tyr Ile Met Arg Tyr Lys Gln Ser Asp Pro
1               5                   10                  15

Glu Asn Pro Asp Asn Asp Arg Phe Val Leu Ala Lys Arg Leu Ser Phe
            20                  25                  30

Val Asp Val Ala Thr Gly Trp Leu Gly Gln Gly Leu Gly Val Ala Cys
        35                  40                  45

Gly Met Ala Tyr Thr Gly Lys Tyr Phe Asp Arg Ala Ser Tyr Arg Val
    50                  55                  60

Phe Cys Leu Met Ser Asp Gly Glu Ser Ser Glu Gly Ser Val Trp Glu
65                  70                  75                  80

Ala Met Ala Phe Ala Ser Tyr Tyr Ser Leu Asp Asn Leu Val Ala Ile
                85                  90                  95

Phe Asp Val Asn Arg Leu Gly His Ser Gly Ala Leu Pro Ala Glu His
            100                 105                 110

Cys Ile Asn Ile Tyr Gln Arg Arg Cys Glu Ala Phe Gly Trp Asn Thr
        115                 120                 125

Tyr Val Val Asp Gly Arg Asp Val Glu Ala Leu Cys Gln Val Phe Trp
    130                 135                 140

Gln Ala Ser Gln Val Lys His Lys Pro Thr Ala Val Val Ala Lys Thr
145                 150                 155                 160

Phe Lys Gly Arg Gly Thr Pro Ser Ile Glu Asp Ala Glu Ser Trp His
                165                 170                 175

Ala Lys Pro Met Pro Arg Glu Arg Ala Asp Ala Ile Ile Lys Leu Ile
            180                 185                 190
```

-continued

| | | | | | | | | | | | | |
|---|---|---|---|---|---|---|---|---|---|---|---|---|
|Glu|Ser|Gln|Ile|Gln|Thr|Ser|Arg|Asn|Leu|Asp|Pro|Gln|Pro|Ile|
| |   |195|   |   |   |   |200|   |   |   |   |205|   |   |

Glu Ser Gln Ile Gln Thr Ser Arg Asn Leu Asp Pro Gln Pro Ile
            195                 200             205

Glu Asp Ser Pro Glu Val Asn Ile Thr Asp Val Arg Met Thr Ser Pro
210             215             220

Pro Asp Tyr Arg Val Gly Asp Lys Ile Ala Thr Arg Lys Ala Cys Gly
225             230             235             240

Leu Ala Leu Ala Lys Leu Gly Tyr Ala Asn Asn Arg Val Val Val Leu
            245             250             255

Asp Gly Asp Thr Arg Tyr Ser Thr Phe Ser Glu Ile Phe Asn Lys Glu
            260             265             270

Tyr Pro Glu Arg Phe Ile Glu Cys Phe Met Ala Glu Gln Asn Met Val
            275             280             285

Ser Val Ala Leu Gly Cys Ala Ser Arg Gly Arg Thr Ile Ala Phe Ala
290             295             300

Ser Thr Phe Ala Ala Phe Leu Thr Arg Ala Phe Asp His Ile Arg Ile
305             310             315             320

Gly Gly Leu Ala Glu Ser Asn Ile Asn Ile Ile Gly Ser His Cys Gly
            325             330             335

Val Ser Val Gly Asp Asp Gly Ala Ser Gln Met Ala Leu Glu Asp Ile
            340             345             350

Ala Met Phe Arg Thr Ile Pro Lys Cys Thr Ile Phe Tyr Pro Thr Asp
            355             360             365

Ala Val Ser Thr Glu His Ala Val Ala Leu Ala Ala Asn Ala Lys Gly
            370             375             380

Met Cys Phe Ile Arg Thr Thr Arg Pro Glu Thr Met Val Ile Tyr Thr
385             390             395             400

Pro Gln Glu Arg Phe Glu Ile Gly Gln Ala Lys Val Leu Arg His Cys
            405             410             415

Val Ser Asp Lys Val Thr Val Ile Gly Ala Gly Ile Thr Val Tyr Glu
            420             425             430

Ala Leu Ala Ala Ala Asp Glu Leu Ser Lys Gln Asp Ile Phe Ile Arg
            435             440             445

Val Ile Asp Leu Phe Thr Ile Lys Pro Leu Asp Val Ala Thr Ile Val
            450             455             460

Ser Ser Ala Lys Ala Thr Glu Gly Arg Ile Ile Thr Val Glu Asp His
465             470             475             480

Tyr Pro Gln Gly Gly Ile Gly Glu Ala Val Cys Ala Ala Val Ser Met
            485             490             495

Asp Pro Asp Ile Gln Val His Ser Leu Ala Val Ser Gly Val Pro Gln
            500             505             510

Ser Gly Lys Ser Glu Glu Leu Leu Asp Met Tyr Gly Ile Ser Ala Arg
            515             520             525

His Ile Ile Val Ala Val Lys Cys Met Leu Leu Asn
530             535             540

<210> SEQ ID NO 5
<211> LENGTH: 958
<212> TYPE: DNA
<213> ORGANISM: Homo sapien
<220> FEATURE:
<221> NAME/KEY: CDS
<222> LOCATION: (3)...(438)

-continued

```
<400> SEQUENCE: 5 gg cgt atc cat gct cca gga cag ctg gag cag tgt aat ttc cta tca       47
   Arg Ile His Ala Pro Gly Gln Leu Glu Gln Cys Asn Phe Leu Ser
    1               5                  10                  15 aaa gtc ctc cgc cac tgt gtc agt gac aag gtc aca gtt att gga gct       95
Lys Val Leu Arg His Cys Val Ser Asp Lys Val Thr Val Ile Gly Ala
                 20                  25                  30 gga att act gtg tat gaa gcc tta gca gct gct gat gag ctt tcg aaa      143
Gly Ile Thr Val Tyr Glu Ala Leu Ala Ala Ala Asp Glu Leu Ser Lys
             35                  40                  45 caa gat att ttt atc cgt gtc atc gac ctg ttt acc att aaa cct ctg      191
Gln Asp Ile Phe Ile Arg Val Ile Asp Leu Phe Thr Ile Lys Pro Leu
         50                  55                  60 gat gtc gcc acc atc gtc tcc agt gca aaa gcc aca gag ggc cgg atc      239
Asp Val Ala Thr Ile Val Ser Ser Ala Lys Ala Thr Glu Gly Arg Ile
     65                  70                  75 att aca gtg gag gat cac tac ccg caa ggt ggc atc ggg gaa gct gtc      287
Ile Thr Val Glu Asp His Tyr Pro Gln Gly Gly Ile Gly Glu Ala Val
 80                  85                  90                  95 tgc gca gcc gtc tcc atg gat cct gac att cag gtt cat tcg ctg gca      335
Cys Ala Ala Val Ser Met Asp Pro Asp Ile Gln Val His Ser Leu Ala
                100                 105                 110 gtg tcg gga gtg ccc cag agt ggg aag tcc gag gaa ttg ctg gat atg      383
Val Ser Gly Val Pro Gln Ser Gly Lys Ser Glu Glu Leu Leu Asp Met
            115                 120                 125 tat gga att agt gcc aga cat atc ata gtg gcc gtg aaa tgc atg ttg      431
Tyr Gly Ile Ser Ala Arg His Ile Ile Val Ala Val Lys Cys Met Leu
        130                 135                 140 ctg aac t aaatagctg ttagccttgg tcttttggcc tctttaccct gtgtttatgt     488
Leu Asn
    145 ttgttccaaa accatcattt aaatctctac tgtcacattt tgtttcttaa aagcaaagcc    548 agctaacacc ttcattcatc cctagttcgg aaattcaagc taactactta ccctttaaac    608 tgtcactgca tatgcaagta ccgctctaat ttttggatca ttaaagggag ttacacaact    668 tttaagtgaa aaaaataggt aacaaaacaa ccacctgata gtaagttttc tgataagact    728 atagataagt ggtagaggta atcaattctt ccgaagtgtt tccttcgtga ataactggta    788 gaggtaatag ttttttcaat gtatttcctt catgagtaaa gaaaatgtgg attgaagtat    848 agattccagt agcctagttt ccacagcacg ataacaccat gacgcctact gctgttccca    908 ccttgggatt ctgtgtgctg ccatcccacc tgcagctgcc ctggaattcc                958

<210> SEQ ID NO 6
<211> LENGTH: 145
<212> TYPE: PRT
<213> ORGANISM: Homo sapien

<400> SEQUENCE: 6

Arg Ile His Ala Pro Gly Gln Leu Glu Gln Cys Asn Phe Leu Ser Lys
 1               5                  10                  15

Val Leu Arg His Cys Val Ser Asp Lys Val Thr Val Ile Gly Ala Gly
             20                  25                  30

Ile Thr Val Tyr Glu Ala Leu Ala Ala Ala Asp Glu Leu Ser Lys Gln
         35                  40                  45

Asp Ile Phe Ile Arg Val Ile Asp Leu Phe Thr Ile Lys Pro Leu Asp
     50                  55                  60
```

-continued

```
Val Ala Thr Ile Val Ser Ser Ala Lys Ala Thr Glu Gly Arg Ile Ile
65                  70                  75                  80

Thr Val Glu Asp His Tyr Pro Gln Gly Gly Ile Gly Glu Ala Val Cys
                85                  90                  95

Ala Ala Val Ser Met Asp Pro Asp Ile Gln Val His Ser Leu Ala Val
                100             105                 110

Ser Gly Val Pro Gln Ser Gly Lys Ser Glu Glu Leu Leu Asp Met Tyr
            115                 120                 125

Gly Ile Ser Ala Arg His Ile Ile Val Ala Val Lys Cys Met Leu Leu
        130                 135                 140

Asn
145

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
cagagatcta tgaggtacaa gcagtcag                                           28

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
gggaagcttt tagttcagca acatgc                                             26

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
cagagatcta tgtggcgtat ccatgc                                             26
```

TRANSKETOLASE-RELATED PROTEIN

This is a national phase filing of the Application No. PCT/DE96/01401, which was filed with the Patent Corporation Treaty on Jul. 26, 1996, and is entitled to priority of the German Patent Application P 195 27 552.7 filed Jul. 27, 1995.

I. FIELD OF THE INVENTION

The present invention relates to a transketolase-related protein, a DNA encoding the same and a process for the preparation thereof. In addition, this invention concerns the use of the DNA and the protein as well as antibodies directed against the protein.

II. BACKGROUND OF THE INVENTION

Transketolase is a thiamine-dependent enzyme which links the pentose phosphate pathway with the glycolysis. The pentose phosphate pathway provides sugar phosphates and NADPH. Transketolase introduces excess sugar phosphates into the glycolysis to as to ensure the provision of NADPH under various metabolic conditions. NADPH is essential for maintaining glutathione in the brain.

Thiamine deficiency is associated with neurologic diseases such as beriberi and Wernicke-Korsakoff syndrome. Beriberi manifests itself in acute heart failure, whereas the Wernicke-Korsakoff syndrome shows as acute encephalopathy followed by chronic damage of the short-term memory.

Investigations refer to the fact that thiamine deficiency is not the cause of the above diseases. Also, no mutated transketolase exists in patients suffering from these diseases, e.g., in patients suffering from the Wernicke-Korsakoff syndrome. Thus, the cause of the above diseases is not known by now.

Therefore, it is the object of the present invention to provide a product by which neurologic diseases associated with thiamine deficiency, particularly beriberi and Wernicke-Korsakoff syndrome, can be investigated as regards their cause and optionally be treated.

III. SUMMARY OF THE INVENTION

The present invention relates to a transketolase-related protein, a DNA encoding the same and a process for the preparation thereof. In addition, the invention concerns the use of the DNA and the protein as well as antibodies directed against the protein.

IV. BRIEF DESCRIPTION OF THE DRAWINGS

FIG. 1 shows the base sequence (SEQ ID NO:1) and the amino acid sequence (SEQ ID NOS:2), derived therefrom, of a (TVP) according to the invention.

FIG. 2 shows the base sequence (SEQ ID NO:3) and the amino acid sequence (SEQ ID NO:4), derived therefrom, of a brain-specific (TVP) according to the invention (arrows indicate the position of (TVP) of FIG. 1).

FIG. 3 shows the base sequence (SEQ ID NO:5) and the amino acid sequence (SEQ ID NO:6), derived therefrom, of a heart-specific (TVP) according to the invention (arrows indicate the position of (TVP) of FIG. 1).

V. DETAILED DESCRIPTION OF THE INVENTION

It is the object of the present invention to provide a product by which neurologic diseases associated with thiamine deficiency, particularly beriberi and Wernicke-Korsakoff syndrome, can be investigated as regards their cause and optionally be treated. According to the invention, this is achieved by the subject matters defined in the claims.

Thus, the subject matter of the present invention relates to a transketolase-related protein, the protein comprising at least the amino acid sequence of FIG. 1 or an amino acid sequence differing therefrom by one or more amino acids.

The present invention is based on the applicant's finding that in animals, particularly mammals, more particularly human beings, there exists a protein which has homologies with respect to a transketolase, optionally a transketolase activity, but differs from a transketolase on the DNA level by hybridization under normal conditions. Such a protein comprises at least the amino acid sequence of FIG. 1 or an amino acid sequence differing therefrom by one or more amino acids. In addition, the protein is present in various tissues, e.g., brain and heart, in differing form.

The above protein is referred to as "transketolase-related protein" (TVP) in the present invention.

In a preferred embodiment, a (TVP) comprises the amino acid sequence of FIG. 2. Such a (TVP) is found especially in the brains of animals, particularly mammals, more particularly human beings.

In a further preferred embodiment, a (TVP) includes the amino acid sequence of FIG. 3. Such a (TVP) is found especially in the hearts of animals, particularly mammals, more particularly human beings.

A further subject matter of the present invention relates to a nucleic acid coding for a (TVP). It may be an RNA or a DNA. The latter may be, e.g., a genomic DNA or a cDNA. Preferred is a DNA which comprises the following:

(a) the DNA of FIG. 1 or a DNA differing therefrom by one or more base pairs, (b) a DNA hybridizing with the DNA of (a), or (c) a DNA related to the DNA of (a) or (b) via the degenerated genetic code.

The expression "hybridizing DNA" refers to a DNA which hybridizes with a DNA of (a) under normal conditions, particularly at 20° C. below the melting point of the DNA.

The DNAs of FIG. 2 and FIG. 3 are especially preferred. The DNA of FIG. 2 codes for a (TVP) which is present especially in the brains of animals, particularly mammals, more particularly human beings. The DNA of FIG. 3 codes for a (TVP) which is present especially in the hearts of animals, particularly mammals, more particularly human beings. The DNA of FIG. 2 was deposited with DSM (Deutsche Sammlung von Mikroorganismen und Zellkulturen [German-type collection of micro-organisms and cell cultures]) as JFC 317 under DSM 9994 on May 23, 1995.

A DNA according to the invention is described below in the form of a cDNA. It is exemplary for every DNA falling under the present invention.

For the preparation of a cDNA according to the invention it is favorable to use a cosmid library, e.g., q1Z (Dietrich et al., 1991, *Nucleic Acids Res.* 19:2567–2572) as a basis, clones of which comprise the region Xq28 of the human genome. Such clones are fixed on a filtering membrane and hybridized with labeled cDNA pools obtained from mRNA of pig tissues, e.g., brain, muscle, liver, heart, by reverse transcription (Coy et al., 1994, *Mammalian Genome* 5:131–137). Those clones which have a hybridization signal with the cDNA pools are used for screening a human cDNA library, e.g., of fetal brain tissue and/or heart tissue. For this purpose, the cDNA libraryλ-Zap, Stratagene Company, catalog No. 936206, is especially suitable. A cDNA according to the invention is obtained.

A cDNA according to the invention can be present in a vector and expression vector, respectively. A person skilled in the art is familiar with examples thereof. In the case of an expression vector for *E. coli* these are, e.g., pGEMEX, pUC derivatives, pGEX-2T, pET3b and pQE-8, the latter being preferred. For the expression in yeast, e.g., pYlOO and Ycpadl have to be mentioned while, e.g., pKCR, pEFBOS, cDM8 and pCEV4 have to be indicated for the expression in animal cells. The baculovirus expression vector pAcSGHisNT-A is especially suitable for the expression in insect cells.

The person skilled in the art knows suitable cells to express a cDNA according to the invention, which is present in an expression vector. Examples of such cells comprise the *E. coli* strains HB101, DH1, x1776, JM101, JM109, BL21 and SG 13009, the latter being preferred, the yeast strain saccharomyces cerevisiae and the animal cells L, 3T3, FM3A, CHO, COS, Vero and HeLa as well as the insect cells sf9.

The person skilled in the art knows in which way a cDNA according to the invention has to be inserted in an expression vector. He is also familiar with the fact that this DNA can be inserted in combination with a DNA coding for another protein and peptide, respectively, so that the cDNA according to the invention can be expressed in the form of a fusion protein.

Furthermore, the person skilled in the art knows conditions of cultivating transformed cells and transfected cells, respectively. He is also familiar with processes of isolating and purifying the protein expressed by the cDNA according to the invention. Thus, such a protein, which may also be a fusion protein, also represents a subject matter of the present invention.

Another subject matter of the present invention relates to an antibody directed against an above protein and fusion protein, respectively. Such an antibody can be prepared by common methods. It may be polyclonal and monoclonal, respectively. For its preparation, it is favorable to immunize animals—particularly rabbits or chickens for a polyclonal antibody and mice for a monoclonal antibody—with an above (fusion) protein or with fragments thereof.

Further "boosters" of the animals may be effected with the same (fusion) protein or with fragments thereof. The polyclonal antibody may then be obtained from the animal serum and egg yolk, respectively. As regards the monoclonal antibody, animal spleen cells are fused with myeloma cells.

The present invention enables to investigate the cause of neurologic diseases associated with thiamine deficiency such as beriberi and Wernicke-Korsakoff syndrome. (TVP) can be detected in the persons' body fluids by an antibody according to the invention. A relation can be established between (TVP) and the development and formation of the above diseases. In addition, an autoantibody directed against this protein can be detected by a (TVP) according to the invention. Both detections can be made by common methods, particularly a Western blot, an ELISA, an immunoprecipitation or by immunofluorescence. Moreover, the expression of the gene coding for (TVP) can be detected by a nucleic acid according to the invention, particularly a DNA and primers derived therefrom. This detection can take place as usual, particularly in a Southern blot.

Besides, the present invention is suitable to take measures for and against the presence of (TVP) in persons. (TVP) can be inhibited in persons by means of an antibody according to the invention. On the other hand, the amount of (TVP) in persons can be increased by a (TVP) according to the invention, particularly after linkage to a protein which is not considered foreign by the body, e.g., transferrin or BSA. The same can also be achieved correspondingly by a nucleic acid according to the invention, particularly a DNA, which is controlled by a promoter inducible in certain tissues, e.g., brain, heart, and which after its expression results in the provision of (TVP) in these tissues. In addition, a nucleic acid according to the invention, particularly a DNA, can also be used for inhibiting (TVP). For this purpose, the nucleic acid is used, e.g., as a basis for preparing anti-sense oligonucleotides for the expression inhibition of the gene coding for (TVP).

Thus, the present invention represents a major contribution to the diagnostic and therapeutic detection of neurologic diseases associated with thiamine deficiency, particularly beriberi and Wernicke-Korsakoff syndrome.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1: Preparation and Purification of a (TVP) According to the Invention For the preparation of a (TVP) according to the invention, the DNAs of FIG. 2 and FIG. 3, respectively, were used as a template. A PCR method was carried out. As far as the DNA of FIG. 2 is concerned, the following primer pair was used: 5'-CAGAGATCTATGAGGTACAAGCAGTCAG-3' (SEQ ID NO:7) and 5'-GGGAAGCTTTTAGTTCAGCAACATGC-3' (SEQ ID NO:8).

As far as the DNA of FIG. 3 is concerned, the following primer pair was used: 5'-CAGAGATCTATGTGGCGTATCCATGC-3' (SEQ ID NO:9) and 5'-GGGAAGCTTTTAGTTCAGCAACATGC-3' (SEQ ID NO:8).

The PCR batch and the PCR conditions were each as follows:

PCR Batch
 template DNA (FIG. 1): 1 $\mu$l=1 ng
 Pfu polymerase 10×buffer: 10 $\mu$l=1 x
 DMSO: 10 $\mu$l=10%
 dNTPs: 1 $\mu$l=200 $\mu$M each
 oligonucleotides, 1.5 $\mu$l each: 3 $\mu$l=150 ng each
 H$_2$O bidistilled: ad 99 $\mu$l PCR Conditions
  92° C. —5 min
  addition of 1 μl Pfu polymerase (Stratagene company)= 2.5 units
  addition of paraffin

| PCR |
|---|
| 92° C. 1 min |
| 58° C. 1 min 1 cycle |
| 72° C. 10 min |
| 92° C. 1 min |
| 58° C. 1 min 39 cycles |
| 72° C. 2 min |
| 72° C. 10 min 1 cycle |

The amplified DNA was cleaved by Bgl II and Hind III each and inserted in the expression vector pQE-8 (Quiagen company) cleaved by Bgl II and Hind III. The expression plasmnid pQ/TVP-G (pQ/TVP-H) was obtained. Such a plasmid codes for a fusion protein comprising 6 histidine residues (N terminus partner) and the (TVP) of FIG. 2 (FIG. 3) according to the invention (C terminus partner). pQ/TVP-G (pQ/TVP-H) was used for transforming *E. coli* SG 13009. Gottesman et al., 1981. *J. Bacteriol.* 148:265–273. The bacteria were cultivated in an LB broth with 100 μg/ml ampicillin and 25 μg/ml kanamycin, and induced with 60 μM isopropyl-β-D-thiogalactopyranoside (IPTG) for 4 h. Lysis of the bacteria was achieved by the addition of 6 M guanidine hydrochloride. Thereafter, chromatography (Ni-NTA resin) was carried out with the lysate in the presence of 8 M urea in accordance with the instructions from the manufacturer (Quiagen company) of the chromatography material. The bound fusion protein was eluted in a buffer having a pH of 3.5. After its neutralization, the fusion protein was subjected to 18% SDS polyacrylamide gel electrophoresis and dyed with coomassie blue. Thomas and Kornberg, 1975, *J. Mol. Biol.* 149:709–733.

It showed that a (fusion) protein according to the invention can be prepared in highly pure form.

B. Example 2: Preparation and Detection of an Antibody According to the Invention A fusion protein of Example 1 according to the invention was subjected to 18% SDS polyacrylamide gel electrophoresis. After dyeing the gel with 4 M sodium acetate, an about 59 (16.5) kD band was cut out of the gel and incubated in phosphate-buffered salt solution. Gel pieces were sedimented before the protein concentration of the supernatant was determined by SDS polyacrylamide gel electrophoresis which was followed by coomassie blue dyeing. Animals were immunized with the gel-purified fusion protein as follows:

1. Immunization Protocol for Polyclonal Antibodies in Rabbits

35 μg of gel-purified fusion protein in 0.7 ml PBS and 0.7 ml of complete Freund's adjuvant and incomplete Freund's adjuvant, respectively, were used per immunization.

Day 0: 1st immunization (complete Freund's adjuvant)
Day 14: 2nd immunization (incomplete Freund's adjuvant; icFA)
Day 28: 3rd immunization (icFA)
Day 56: 4th immunization (icFA)
Day 80: bleeding to death.

The rabbit serum was tested in an immunoblot. For this purpose, a fusion protein of Example 1 according to the invention was subjected to SDS polyacrylamide gel electrophoresis and transferred to a nitrocellulose filter. Khyse-Andersen, 1984, *Biochem. Biophys. Meth.* 10:203–209. The Western blot analysis was carried out as described in Bock et al., 1994, *Virus Genes* 8:215–229. For this purpose, the nitrocellulose filter was incubated with a first antibody at 37° C. for one hour. This antibody was the rabbit serum (1:10000 in PBS). After several wash steps using PBS, the nitrocellulose filter was incubated with a second antibody. This antibody was an alkaline phosphatase-coupled monoclonal goat anti-rabbit IgG antibody (Dianova company) (1:5000) in PBS. 30 minutes of incubation at 37° C. were followed by several wash steps using PBS and then by the alkaline phosphatase detection reaction with developer solution (36 μM 5'-bromo-4-chloro-3-indolyl phosphate, 400 μM nitroblue tetrazolium, 100 mM tris-HCl, pH. 9.5, 100 mM NaCl, 5 mM $MgCl_2$) at room temperature, until bands were visible.

It showed that polyclonal antibodies according to the invention can be prepared.

2. Immunization Protocol for Polyclonal Antibodies in Chickens

40 μg of gel-purified fusion protein in 0.8 ml PBS and 0.8 ml of complete Freund's adjuvant and incomplete Freund's adjuvant, respectively, were used per immunization.

Day 0: 1st immunization (complete Freund's adjuvant)
Day 28: 2nd immunization (incomplete Freund's adjuvant; icFA)
Day 50: 3rd immunization (icFA)

Antibodies were extracted from egg yolk and tested in a Western blot. Polyclonal antibodies according to the invention were detected.

3. Immunization Protocol for Monoclonal Antibodies in Mice

12 μg of gel-purified fusion protein in 0.25 ml PBS and 0.25 ml of complete Freund's adjuvant and incomplete Freund's adjuvant, respectively, were used per immunization. The fusion protein was dissolved in 0.5 ml (without adjuvant) in the 4th immunization.

Day 0: 1st immunization (complete Freund's adjuvant)
Day 28: 2nd immunization (incomplete Freund's adjuvant; icFA)
Day 56: 3rd immunization (icFA)
Day 84: 4th immunization (PBS)
Day 87: fusion Supernatants of hybridomas were tested in a Western blot. Monoclonal antibodies according to the invention were detected.

All references cited within the body of the instant specification are hereby incorporated by reference in their entirety.

What is claimed:

1. An isolated transketolase-related protein, wherein the protein comprises the amino acid sequence of FIG. 1 (SEQ ID NO:2).

2. The protein of claim 1, wherein the protein comprises the amino acid sequence of FIG. 2 (SEQ ID NO:4).

3. The protein of claim 1, wherein the protein comprises the amino acid sequence of FIG. 3 (SEQ ID NO:6).

4. An isolated nucleic acid sequence encoding the protein of claim 1, 2, or 3.

5. An isolated polynucleotide comprising the nucleic acid sequence of FIG. 1 (SEQ ID NO: 1).

6. An isolated polynucleotide comprising the nucleic acid sequence of FIG. 2 (SEQ ID NO:3).

7. An isolated polynucleotide comprising the nucleic acid sequence of FIG. 3 (SEQ ID NO:5).

8. An expression plasmid, comprising the nucleic acid sequence of claim 4.

9. A transformant comprising the expression plasmid of claim 8.

10. A process for the preparation of a transketolase-related protein, comprising the cultivation of the transformant of claim 9 under suitable conditions.

11. A composition comprising the protein of claim 1, 2, or 3.

12. A composition comprising the DNA of claim 4 and/or treatment.

13. An expression plasmid, comprising the nucleic acid sequence of claim 5, 6, or 7.

14. A transformant comprising the expression plasmid of claim 13.

15. A process for the preparation a trarsketolase-related protein, comprising the cultivation of the transformant according to claim 14 under suitable conditions.

16. A composition comprising the DNA of claim 5, 6, or 7.

* * * * *